United States Patent
Imbruce et al.

(10) Patent No.: US 10,926,113 B2
(45) Date of Patent: *Feb. 23, 2021

(54) PORTABLE CHEMICAL OXYGEN GENERATOR

(71) Applicant: Rapid Oxygen Company Inc., Stamford, CT (US)

(72) Inventors: Richard P. Imbruce, Westport, CT (US); David Cowan, Cornwall, CT (US)

(73) Assignee: Rapid Oxygen Company, Inc., Stamford, CT (US)

(*) Notice: Subject to any disclaimer, the term of this patent is extended or adjusted under 35 U.S.C. 154(b) by 370 days.

This patent is subject to a terminal disclaimer.

(21) Appl. No.: 15/811,148

(22) Filed: Nov. 13, 2017

(65) Prior Publication Data
US 2018/0154192 A1 Jun. 7, 2018

Related U.S. Application Data

(63) Continuation of application No. 15/366,891, filed on Dec. 1, 2016, now Pat. No. 9,849,312.

(51) Int. Cl.
*A62B 7/08* (2006.01)
*A61M 16/10* (2006.01)
(Continued)

(52) U.S. Cl.
CPC ........... *A62B 7/08* (2013.01); *A61M 16/0666* (2013.01); *A61M 16/0808* (2013.01);
(Continued)

(58) Field of Classification Search
CPC ............................. A61M 16/1005; A62B 7/08
See application file for complete search history.

(56) References Cited

U.S. PATENT DOCUMENTS 4,253,690 A * 3/1981 Hollander ............... F16K 35/00
292/354
4,671,270 A 6/1987 Kato
(Continued)

FOREIGN PATENT DOCUMENTS

EP 2790792 A1 10/2014
GB 20070017478 9/2007
(Continued)

OTHER PUBLICATIONS

International Search Report and Written Opinion issued in corresponding International Application No. PCT/US2017/061376 dated Feb. 2, 2018.

*Primary Examiner* — Sean E Conley
(74) *Attorney, Agent, or Firm* — Smith Patent, LLC; Richard E. Park; Chalin A. Smith

(57) ABSTRACT

A portable chemical oxygen generator for delivering oxygen to a patient is described. The generator includes a housing containing a reaction chamber. Within the reaction chamber is a quantity of a peroxide adduct. A valve is provided with a lower portion of the valve in fluid communication with the reaction chamber. An upper portion of the valve is in fluid communication with a reservoir that holds a quantity of an aqueous solution. An internal chamber is formed within the valve by releasable seals that separate the internal chamber from the upper portion of the valve and a lower portion of the valve. The internal chamber holds a quantity of a peroxide-decomposing catalyst. The generator also includes a valve actuator. Operation of the valve actuator releases the seals in the valve and creates a fluid path from the reservoir through the internal chamber into the reaction chamber. When the valve is actuated, the aqueous solution flows from the reservoir through the internal chamber and into the reaction chamber. This flow washes the catalyst into the reaction chamber along with the aqueous solution. The
(Continued)

solution and catalyst mix with the peroxide adduct and cause an oxygen-generating reaction.

22 Claims, 16 Drawing Sheets

(51) Int. Cl.
| | |
|---|---|
| A62B 21/00 | (2006.01) |
| C01B 13/02 | (2006.01) |
| C01B 15/022 | (2006.01) |
| A61M 16/20 | (2006.01) |
| A61M 16/06 | (2006.01) |
| A61M 16/08 | (2006.01) |
| A62B 9/02 | (2006.01) |
| A62B 18/02 | (2006.01) |

(52) U.S. Cl.
CPC ...... *A61M 16/1005* (2014.02); *A61M 16/201* (2014.02); *A62B 9/02* (2013.01); *A62B 18/025* (2013.01); *A62B 21/00* (2013.01); *C01B 13/0214* (2013.01); *C01B 15/022* (2013.01); *A61M 2202/0208* (2013.01); *A61M 2205/8231* (2013.01)

(56) References Cited

U.S. PATENT DOCUMENTS

| | | | |
|---|---|---|---|
| 5,620,664 | A | 4/1997 | Palmer |
| 5,823,181 | A | 10/1998 | Shih |
| 6,143,251 | A | 11/2000 | Beller et al. |
| 6,319,477 | B1 | 11/2001 | Du Toit |
| 6,347,627 | B1 | 2/2002 | Frankie et al. |
| 7,165,546 | B2 | 1/2007 | Frankie et al. |
| 7,171,964 | B2 | 2/2007 | Moore et al. |
| 7,225,806 | B2 | 6/2007 | Mawhirt et al. |
| D549,341 | S | 8/2007 | Ross et al. |
| D549,342 | S | 8/2007 | Ross et al. |
| 7,381,377 | B2 | 6/2008 | Ross et al. |
| 7,407,632 | B2 | 8/2008 | Ross |
| 7,465,428 | B2 | 12/2008 | Ross |
| 7,513,251 | B2 | 4/2009 | Blum |
| 7,694,674 | B2 | 4/2010 | Crome et al. |
| D615,186 | S | 5/2010 | Ross et al. |
| 8,147,760 | B1 | 4/2012 | Huvard et al. |
| 8,919,340 | B2 | 12/2014 | Blum |
| 8,944,048 | B2 | 2/2015 | Monzyk |
| 9,028,769 | B2 | 5/2015 | Vigier et al. |
| 9,849,312 | B1 * | 12/2017 | Imbruce .................. A62B 7/08 |
| 2007/0048201 | A1 | 3/2007 | Sagaser |
| 2014/0248195 | A1 | 9/2014 | Vigier et al. |
| 2014/0345610 | A1 | 11/2014 | Unger et al. |
| 2018/0036561 | A1 | 2/2018 | Ward et al. |

FOREIGN PATENT DOCUMENTS

| | | |
|---|---|---|
| WO | WO 2009/030921 A2 | 3/2009 |
| WO | WO 2009/030921 A3 | 3/2009 |
| WO | WO 2013/090935 A1 | 6/2013 |
| WO | WO 2016/149030 A1 | 9/2016 |

* cited by examiner

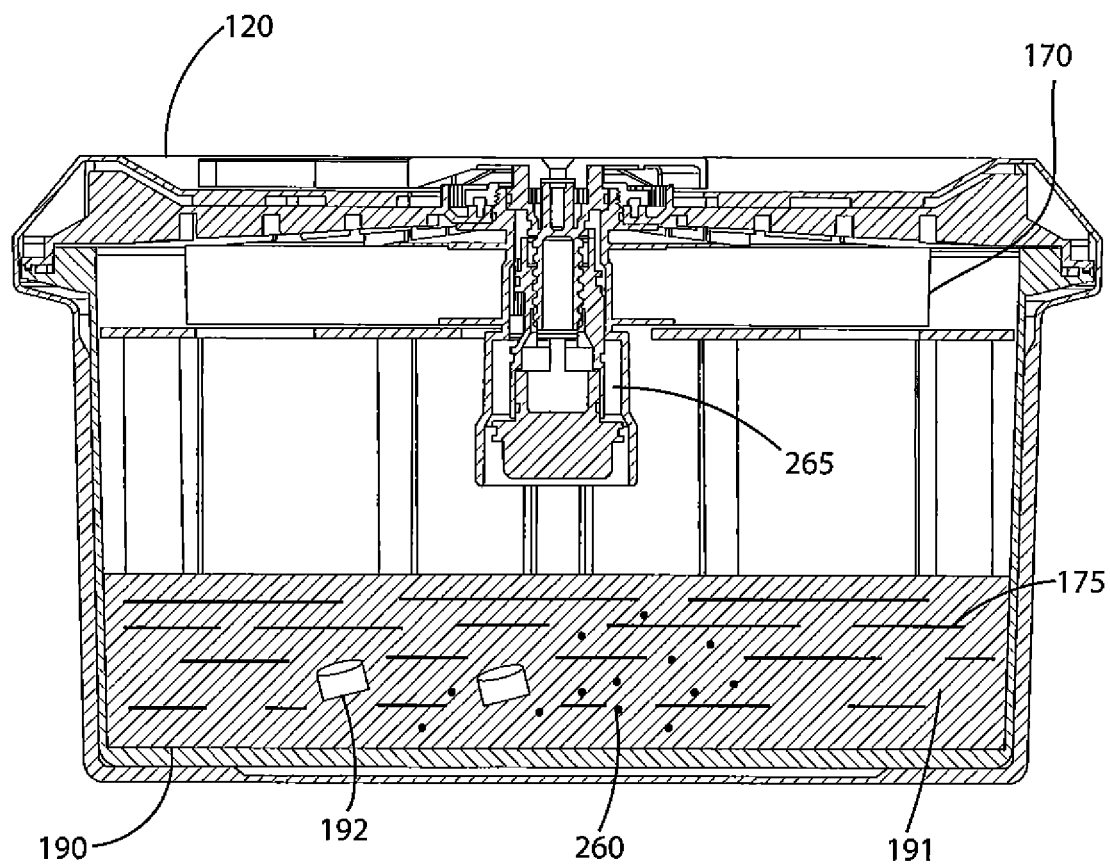

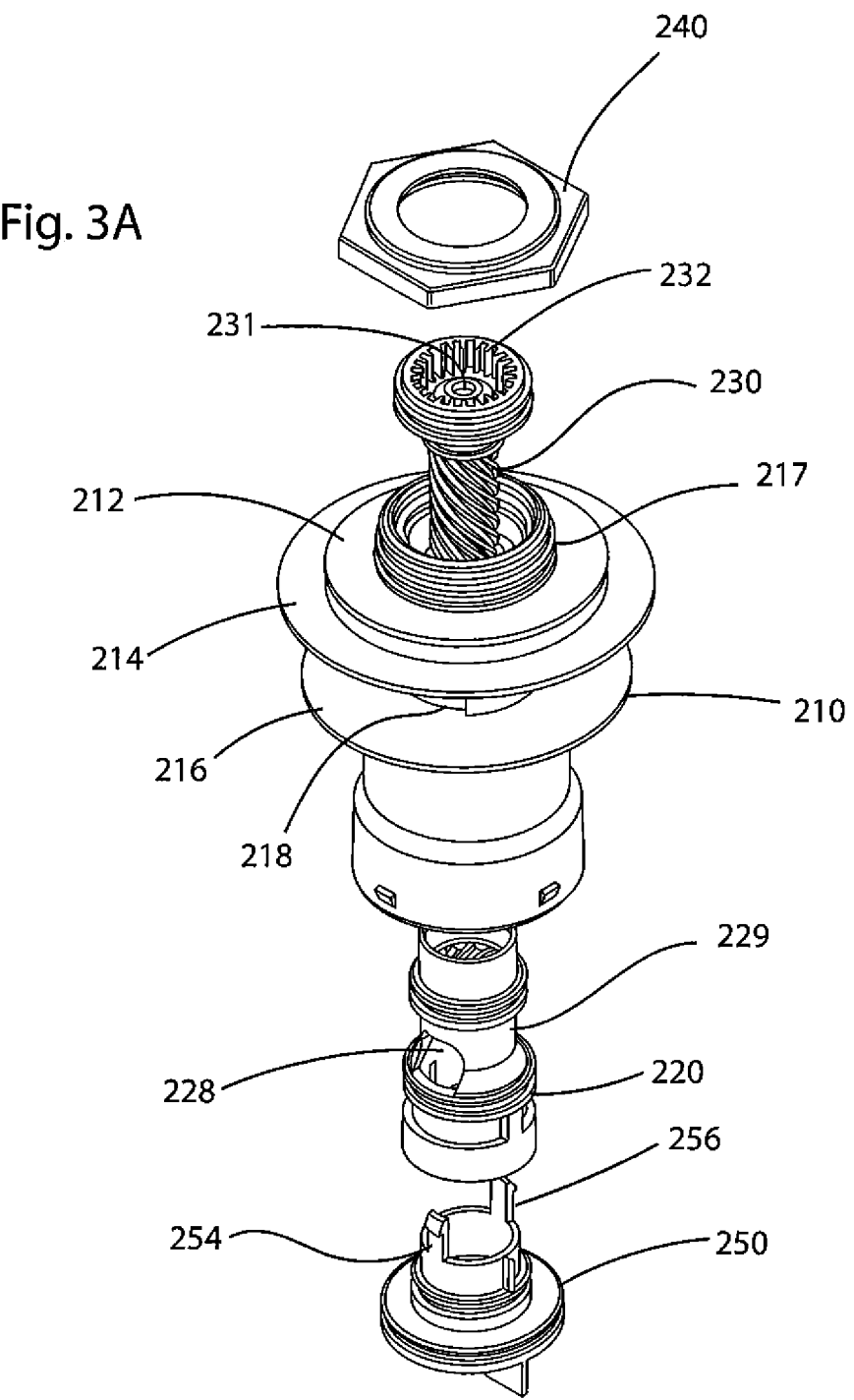

PORTABLE CHEMICAL OXYGEN GENERATOR

This application is a continuation of application Ser. No. 15/366,891 filed Dec. 1, 2016, the entire disclosure of which is incorporated herein by reference

TECHNICAL FIELD

The present application is generally directed to portable chemical oxygen generators and, more particularly, to generators that are capable of producing high-purity oxygen in medical emergencies or other situations in which a reliable and simple-to-operate system is needed.

COPYRIGHT NOTICE

A portion of the disclosure of this patent document contains material subject to copyright protection. The copyright owner has no objection to the facsimile reproduction by anyone of the patent document or the patent disclosure, as it appears in the Patent and Trademark Office patent files or records, but otherwise reserves all copyrights whatsoever.

BACKGROUND OF THE INVENTION

Without breath, life ceases. Oxygen—the second most abundant element in air—is essential for the numerous metabolic processes that sustain human life. While humans can survive without food for weeks and without water for days, survival is counted in minutes if the supply of oxygen ceases. And even if restored, brain damage may result if the oxygen deprivation was too long; the severity increases with each passing minute.

Generally, sources of oxygen for treating acute medical conditions are not readily available for members of the public to help a victim before first responders arrive, and the attendant delay in administering oxygen before such trained help arrives may result in further injury or death. First responders typically arrive with an oxygen source, usually a compressed gas cylinder. Those oxygen cylinders are heavy, cumbersome, costly to transport, and potentially dangerous. For example, the Department of Veterans Affairs warns that an oxygen cylinder can be turned "into a missile" if a cylinder fractures, and the "[e]scaping gas will propel the cylinder with enough force to penetrate cinder block walls." See http://www.patientsafety.va.gov/professionals/hazards/oxygen.asp. Use of gas cylinders requires training to ensure safe and proper administration of gas to a patient—members of the public, for the most part, lack such knowledge.

Other devices for delivering oxygen include oxygen concentrator machines. These devices use electrically-powered mechanisms to separate oxygen from ambient air and deliver an oxygen-rich stream of gas to a patient. Shortcomings for these devices include the fact that they are often quite heavy, require batteries or some other power source, and are noisy. Thus, their use in emergent situations is limited to places where power is available, either to operate the device itself or to keep on-board batteries sufficiently charged. Additionally, as oxygen concentrators depend on the quality of the ambient air, their use is negatively affected in heavily polluted areas. Also, altitude affects the delivery of oxygen from these types of devices.

Another solution to the delivery of oxygen in emergent situations is a chemical oxygen generator, which is a device that releases oxygen via a chemical reaction. One example, sometimes called an "oxygen candle," relies on the combustion of a chemical reaction to release oxygen. The oxygen source is an inorganic superoxide, chlorate, or perchlorate mixed with a combustion agent, such as iron. A firing pin ignites the mixture. And while such devices can deliver oxygen in an emergency, they operate at an extremely high temperature and are potentially a fire hazard. To protect surrounding structures, significant thermal insulation must be provided.

Combustion-driven generators have been around for some time and are still used, for example, in the airline and mining industries. In commercial aircraft, this type of emergency oxygen is available to passengers to protect them from cabin pressure drops (the cockpit crew uses compressed oxygen canisters instead). Modern aircraft systems generally use the decomposition of a mixture of chlorates, perchlorates, and sometimes superoxides that decompose exothermically above 400° C. to produce oxygen and salt. Ignition using an explosive cap causes the dry chemicals to react, resulting in oxygen production. While such systems can reliably produce oxygen for periods of 15 minutes or longer, the storage of explosive and flammable materials on board a commercial aircraft poses significant safety risks. And while the chemical mixtures in these devices can be stored almost indefinitely at both cold and hot temperatures, there have been real world tragedies. For example, on May 11, 1996, accidental ignition of generators in the aircraft's cargo hold caused the ValuJet Flight 592 crash. Ten years earlier, on Aug. 10, 1986, an ATA DC-10 was destroyed while parked at O'Hare Airport due to the accidental activation of an oxygen generator. And on Feb. 24, 1997, a fire broke out on the Russian Mir space station after a cosmonaut ignited an oxygen-producing perchlorate canister to supplement the space station's air supply.

SUMMARY OF THE INVENTION

Accordingly, there is a need for a chemical oxygen generation device that overcomes the deficiencies of known systems. Such a device would be relatively lightweight, not require pressurized gases, produce high-purity oxygen for extended periods of time (e.g., up to 20 minutes), and have a long shelf/storage life. Such a device would also be relatively simple to operate, so that the general public would be able to deliver oxygen in emergent situations before medical personnel arrive. Such a device would also enable the delivery of oxygen in austere conditions (e.g., high altitude, military far-forward areas). Moreover, such a device is desirable in a number of non-critical settings, for example, at sporting events where oxygen-depleted athletes would benefit from supplemental oxygen or in rural areas, where access to other forms of supplemental oxygen may not be available.

The present invention overcomes these and other disadvantages of prior art systems and methods.

According to one embodiment of the invention, a portable oxygen generator includes a housing, a reaction chamber within the housing holding a peroxide adduct, and a valve. A lower portion of the valve is in fluid communication with the reaction chamber. The valve also includes an internal chamber within the valve. The internal chamber is formed by releasable seals separating the internal chamber from the upper portion of the valve and a lower portion of the valve. The internal chamber holds a peroxide-decomposing catalyst. A reservoir holding an aqueous solution is in fluid communication with the upper portion of the valve. The generator also includes a valve actuator. Operation of the valve actuator releases the seals in the valve and creates a fluid path from the reservoir through the internal chamber into the reaction chamber. When the valve is actuated, the aqueous solution flows from the reservoir through the internal chamber, washing the catalyst into the reaction chamber. The aqueous solution and catalyst mix with the peroxide adduct, causing an oxygen-generating reaction.

According to a further embodiment, when the valve is actuated an outlet path for the flow of oxygen generated by the reaction through the valve and out of the device is provided.

According to a further embodiment, the oxygen generator includes a liquid impermeable, gas permeable membrane disposed in the outlet path.

According to a further embodiment, the valve actuator of the oxygen generator includes a threaded, rotatable shaft and the valve includes a threaded valve portion engaged with the threaded rotatable shaft. Rotation of the shaft of the valve actuator causes displacement of the valve, creating a fluid path through the valve. According to yet another embodiment, the valve actuator includes an actuation handle external of the housing and connected with the shaft, wherein movement of the handle causes rotation of the shaft to actuate the valve.

According to a further embodiment, the oxygen generator includes a temperature stabilizing material in the reaction chamber along with the peroxide adduct. According to another embodiment, the temperature stabilizing material includes one or more of a powder, a tablet, and a capsule. According to another embodiment, the temperature stabilizing material may be combined with other compounds, including waxes, e.g., paraffin. These other compounds may be mixed with the powder, incorporated within the tablets or capsules, or provide a coating for the tablets or capsules. According to yet another embodiment, the peroxide adduct includes sodium percarbonate. According to a still further embodiment, the aqueous solution includes water and an anti-freeze substance. According to a yet another embodiment, the catalyst includes manganese dioxide.

According to a further embodiment, the housing of the oxygen generator includes an outer layer where the outer layer is separated from a surface of the housing.

According to a further embodiment, the housing of the oxygen generator includes a pressure relief mechanism.

According to a further embodiment, the oxygen generator includes a condensate trap disposed at an outflow portion of the outlet path.

According to a further embodiment, the valve of the oxygen generator enters the reaction chamber from above after actuation. The reactant chamber is configured with a containment volume, the containment volume being the volume of the reactant chamber in a space below the valve. The generator is configured so that the volume of the aqueous solution, the catalyst, and the peroxide adduct is less than the containment volume.

BRIEF DESCRIPTION OF THE DRAWINGS

The invention is illustrated in the figures of the accompanying drawings, which are meant to be exemplary and not limiting, and in which like references are intended to refer to like or corresponding parts.

FIG. 2C depicts a cross-sectional view of the oxygen delivery system of the present invention, with chemical reactants and water in the device, in the actuated state.

FIG. 3A depicts an exploded view of the valve assembly of the oxygen delivery system of the present invention.

DETAILED DESCRIPTION

A portable oxygen generator and the method of making and using such a generator according to embodiments of the present invention are provided. As described below, the present invention discloses a mechanism whereby a device containing an adduct chemical such as sodium percarbonate ("NaPerc"), which releases oxygen when mixed with water in the presence of a suitable catalyst, e.g., manganese dioxide ("$MnO_2$"), is held in a dry state and separated from the catalyst until such time as oxygen is required. An example of such a time is when intervention in a respiratory-related medical emergency is required, at which point an operator will initiate the process detailed below. Because generating oxygen from such adducts is usually exothermic and usually required over an extended period of time, a reaction-moderating chemical, for example, trisodium phosphate dodecahydrate ("TSP"), may also be provided. This moderating chemical is provided as tablets, capsules, or other agglomerations of certain dimensions mixed with the adduct chemical to facilitate release of the chemical over time. Other sustained-release forms are also within the scope of the invention.

Figure 2A:
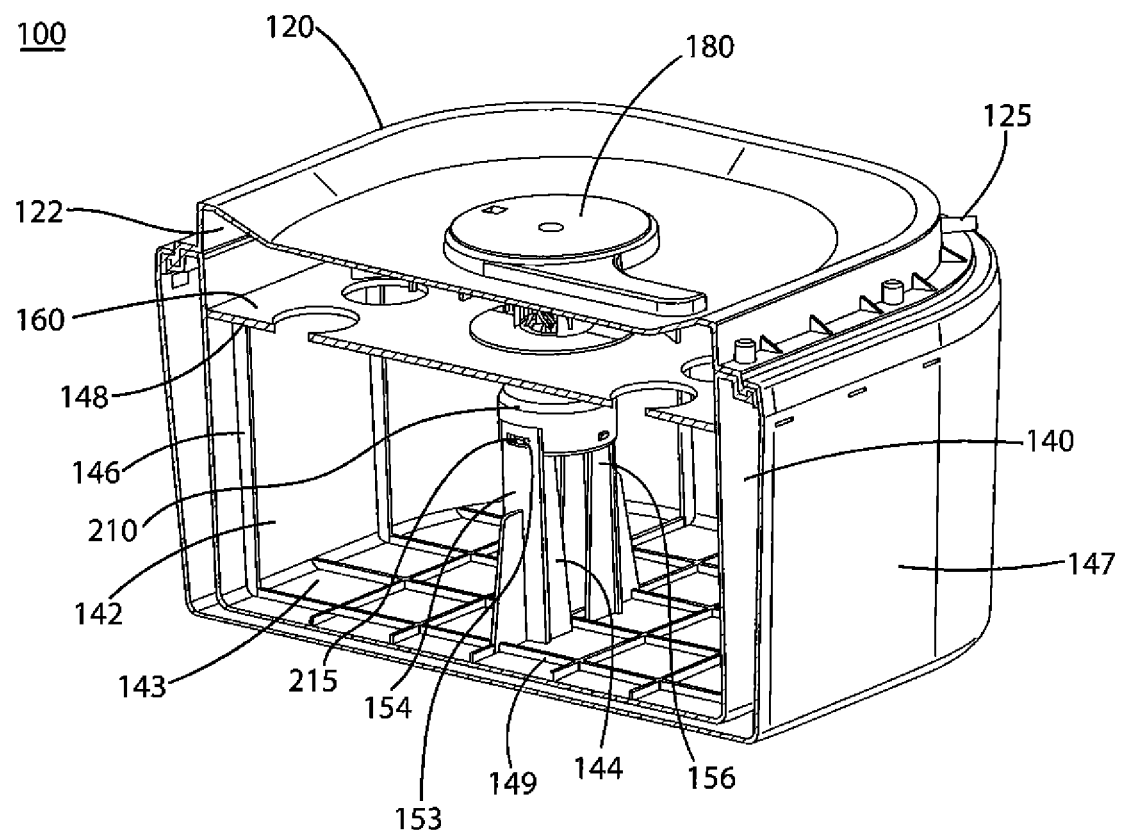
FIG. 2A depicts a cross-sectional view of the oxygen delivery system of the present invention without any chemical reactants or water in the device.
Figure 2B:
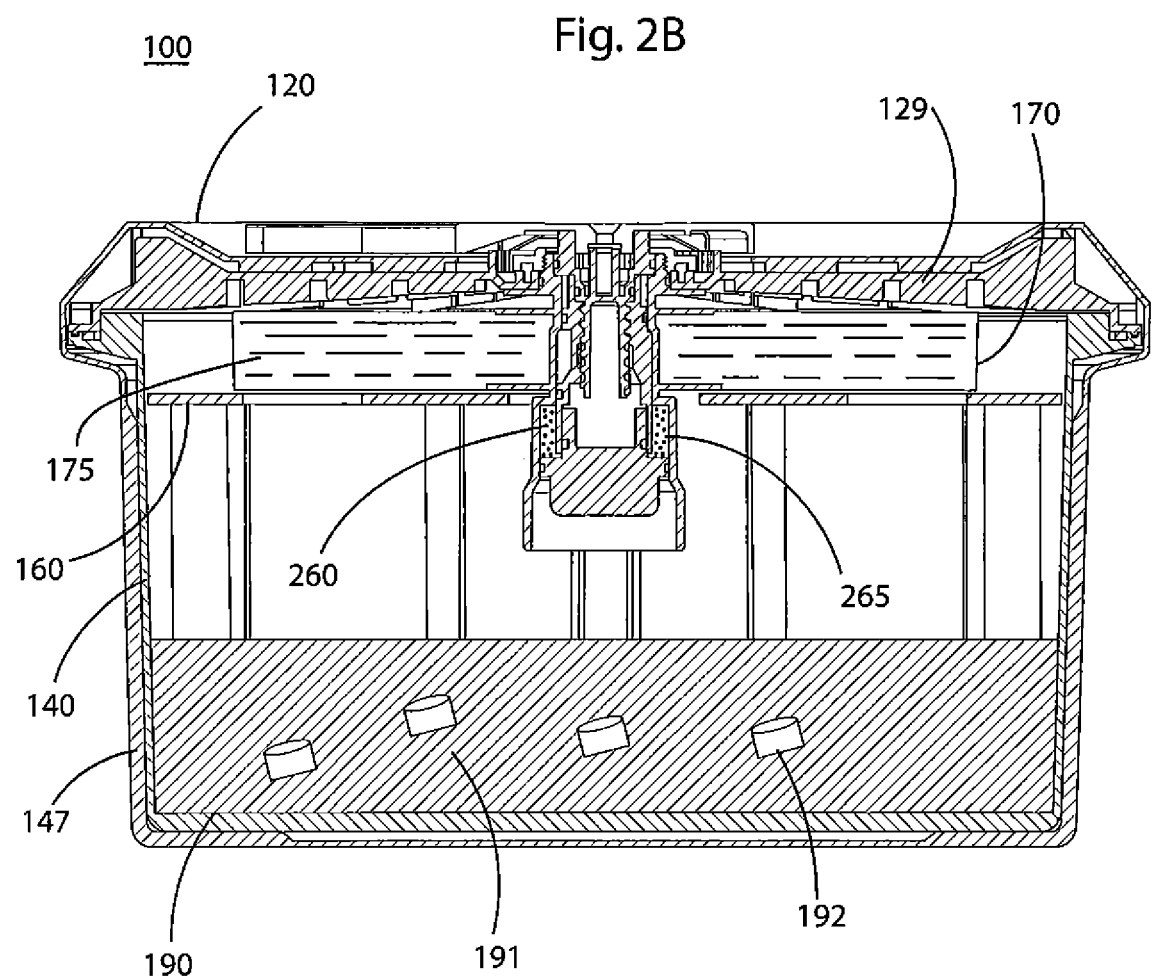
FIG. 2B depicts a cross-sectional view of the oxygen delivery system of the present invention, with chemical reactants and water in the device, in the unactuated state.

A device according to an embodiment of the invention holds water 175 in a water reservoir 170, as shown in FIG. 2B. The water reservoir 170 is in fluid communication with a valve assembly 200. Within the valve assembly 200 is a chamber 265 that is provided to hold the catalyst 260. Below the valve assembly 200 and water reservoir 170 is a housing 140 that holds an oxygen-generating mixture 190 that in an embodiment of the invention is comprised of an adduct chemical 191 mixed with tablets, capsules, and/or powder formed of a moderating chemical 192. In an embodiment of the present invention, the capsules are water-soluble capsules. In another embodiment, the moderating chemical may be combined with other compounds, including waxes, e.g., paraffin. These other compounds may be mixed with the powder, incorporated within the tablets or capsules, or provide a coating for the tablets or capsules.

Figure 6A:
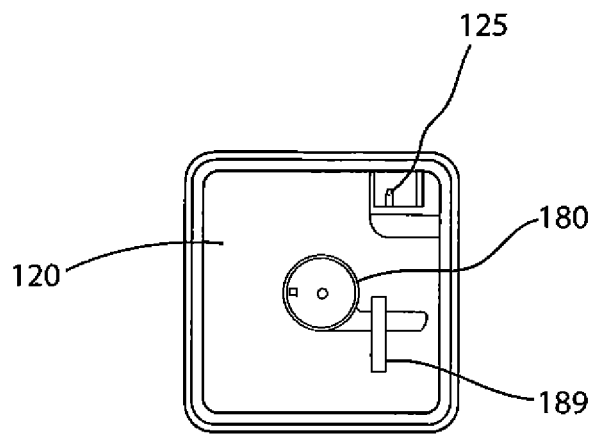
FIG. 6A depicts a top view of the oxygen delivery system of the present invention and further depicts the actuation handle in the unactuated state.

When the valve assembly 200 is actuated by rotation of a handle 180 located at the top surface of the oxygen delivery system 100, water 175 in the water reservoir 170 flows through the valve assembly 200, including through the chamber 265 holding the catalyst 260, and into the housing 140 holding the adduct chemical 191 and moderator 192. By flowing the water 175 through the chamber 265 holding the catalyst 260, the system 100 assures that the entire amount of the catalyst 260 will be delivered to the housing 140 where the oxygen generation reaction will take place. A restraint 189 (see FIG. 6A) between the handle 180 and the lid 120 is removed so that the handle 180 may be activated. In an embodiment of the present invention, the restraint 189 is a tape of a strength that will prevent accidental activation of this one-time-use device but not inhibit activation when generated oxygen is intended or desired. It is important to note that an important purpose of this invention is to be widely available for use, not only in a number of different environments, but also by a number of different operators. Thus, it is a purpose of this invention, and it has been so designed, to allow for a variety of different operators. Accordingly, the actuation handle 180 and the restraint 189 are designed to reduce as much as possible the likelihood of accidental actuation of this single-use-only device while at the same time allowing for operators of varying strength, physical condition, and the like to perform the relatively uncomplicated two-step process of removing (or otherwise overcoming) the restraint 189 and turning the actuation handle 180 from the closed to fully open position, as described below. Consequently, the present invention has been designed for actuation for use by not only fully-abled adults, but also, for example, an older user with arthritis of the hand, wrist, shoulder, or elbow, or a young user incapable of comprehending and completing complicated tasks.

Figure 5:
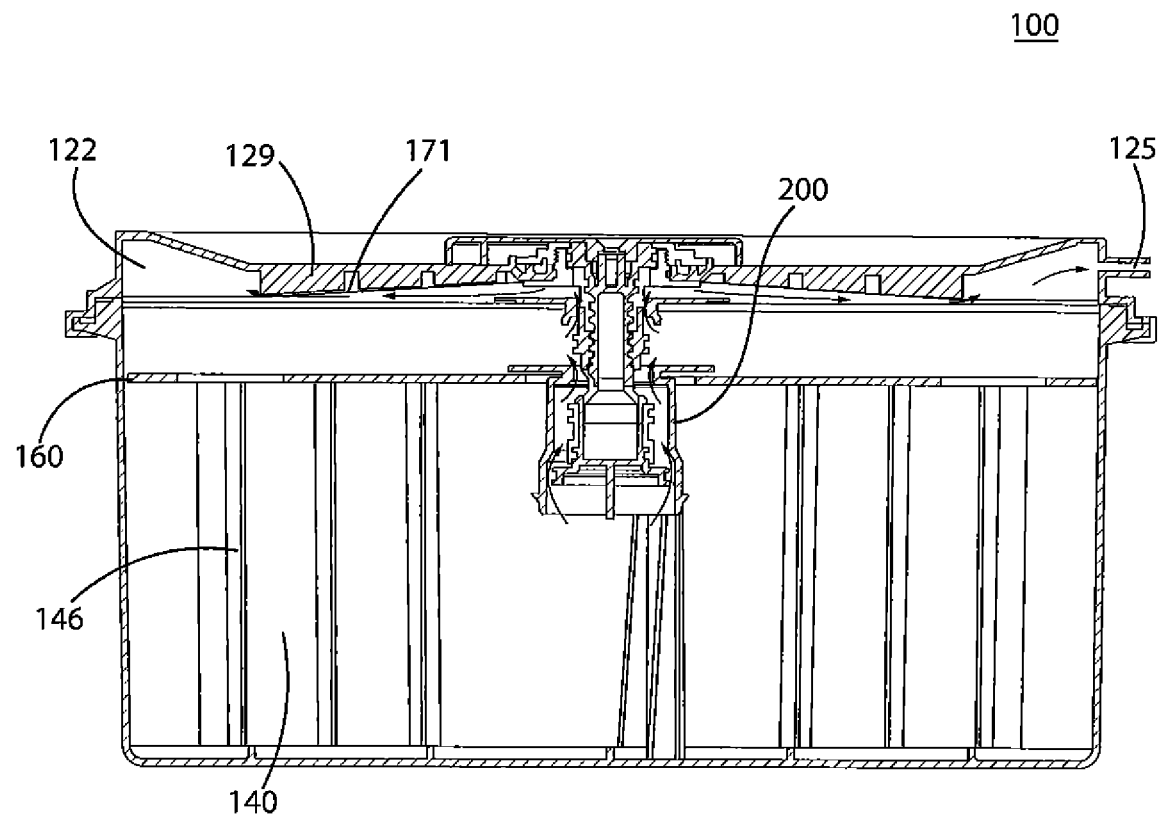
FIG. 5 depicts a cross-sectional view of the oxygen delivery system of the present invention in the actuated state and further depicts the exit path for the generated oxygen.

Once actuated, the valve assembly provides a path for oxygen generated by the reaction to flow upward for delivery to a patient. The upward flow of oxygen is illustrated in FIG. 5. Generated oxygen enters the valve assembly 200 at the bottom and exits the valve assembly 200 above the water reservoir 170. Oxygen flows into a space below a gas-permeable, liquid-impermeable membrane 171 that is disposed above the water reservoir 170 but below the lid 120. The oxygen passes through the membrane 171 and into an oxygen-collecting chamber 122. The chamber 122 is coupled with an outlet port 125. Oxygen can then be delivered to a patient by connecting a hose to a facemask or nasal cannula (not shown).

In one embodiment of the invention, the device has a hose and facemask, or a hose and nasal cannula, that comes pre-connected with the oxygen port 125 on the device 100 so that when there is a need for oxygen generation, the separate step of connecting a hose and facemask for patient use is not necessary. In another embodiment of the invention, the pre-connected hose and facemask or nasal cannula (not shown) are secured to the lid 120 by an attachment means (not shown). In another embodiment of the invention, the hose and facemask or nasal cannula on the lid 120 (not shown) are not pre-connected with the device 100 at the oxygen port 125, but are secured to the lid 120 by an attachment means (not shown).

Figure 1:
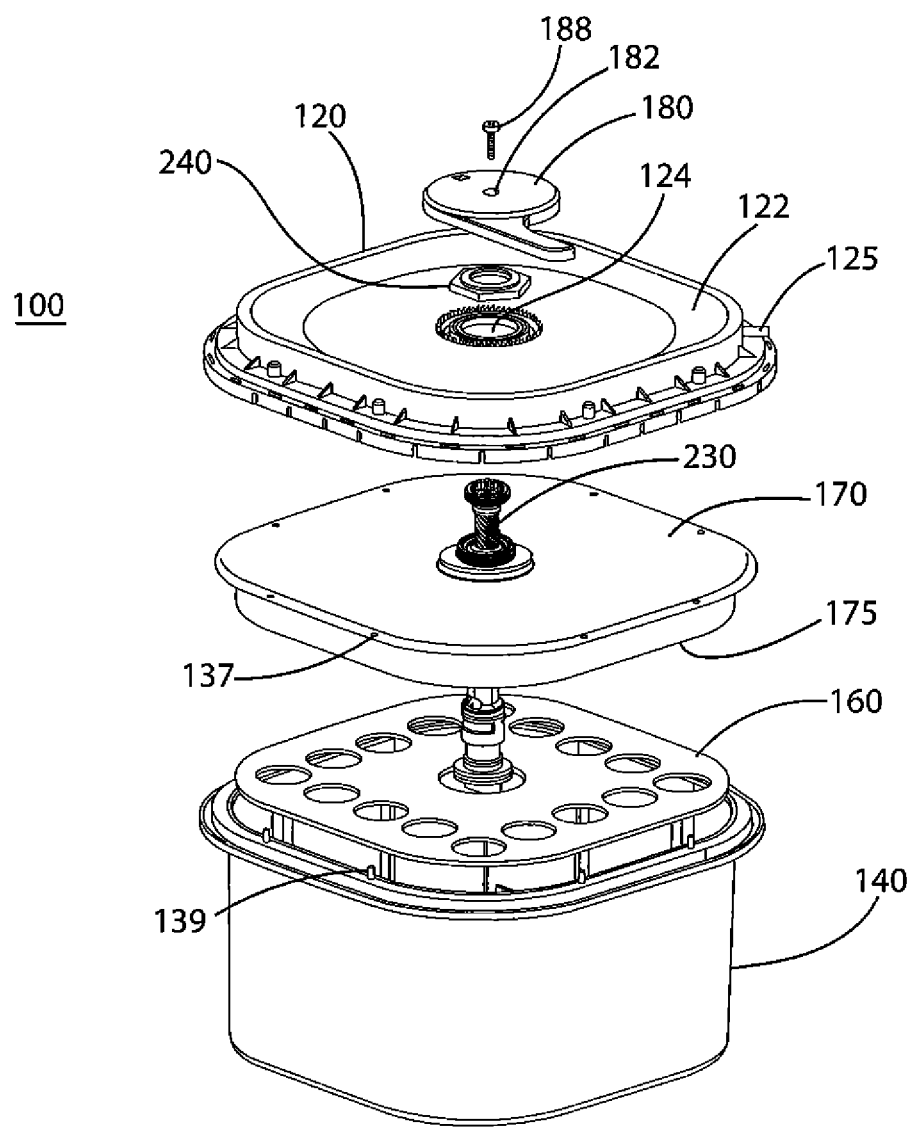
FIG. 1 depicts an exploded view of the oxygen delivery system of the present invention in the unactuated state.

The device 100 will now be discussed. FIG. 1 shows an exploded view of an oxygen delivery system according to an embodiment of the invention. An oxygen delivery system 100 is comprised of a housing lid 120 fitted to a housing 140, which in the FIG. 1 embodiment is an open-faced box. Connected with, and situated between, the lid 120 and the housing 140 is the valve assembly 200.

The lid 120 is designed to engage with the rim of the housing 140 to create a gas- and liquid-tight seal. A pressure relief valve (not shown) is provided to prevent damage to the device from internal pressure if the outlet port 125 becomes clogged or otherwise does not allow oxygen to flow out. According to one embodiment, the maximum pressure above atmospheric pressure is between 0.1 and 40 psi, preferably between 0.8 and 3 psi, and most preferably 1 psi. In one embodiment of the invention, the pressure relief valve (not shown) is provided in the lid 120.

According to the embodiment shown in FIG. 1, the peripheral region of lid 120 is raised, and the volume underneath that region is an oxygen-accumulation chamber 122. Oxygen port 125 connects with the chamber 122. The port 125 also provides an interface for delivering generated oxygen to an individual in need.

The housing 140 may be square, rectangular, circular, or any other shape that will provide sufficient volume to hold the reactant chemicals. The shape of the housing 140 may also be irregular or otherwise shaped to fit within a storage space, such as a storage bay of a vehicle (e.g., an aircraft, ship, train, or the like). The housing 140 and/or the lid 120 may include structures such as a handles (not shown) or straps to secure the device 100 in a storage space. The device 100 may also include loops, buckles, and the like. The housing or lid may also include placards providing instructions for using the device. The housing or lid may be colored to improve the device's visibility (e.g., emergency orange), may include luminescent pigments, or may be painted or otherwise decorated in a manner that will facilitate the device's use in low-light situations.

The interior surface 121 of housing lid 120 has a series of ribs 129 extending downward to provide mechanical strength and, as discussed below, hold the upper surface of the water reservoir 170 and the membrane 171 (see FIG. 5) away from the inner surface 121 of lid 120. This prevents the membrane 171 from adhering to the surface of the lid 120 (e.g., were membrane 171 to become wet), which allows oxygen generated by the device to flow through the chamber 122 to the port 125.

As shown in FIG. 2A, the interior of the housing 140 has walls 142 and a bottom surface 143. A series of spaced-apart ribs 146 run vertically up the walls 142 and along the bottom surface 143. The ribs 146 along the wall 142 extend vertically the same distance from the bottom surface 143 and terminate to form shelves 148 that extend away from the wall 142. There are also a series of bottom-surface ribs 149 extending upward from the bottom surface 142. The ribs 146 and 149 also serve to provide structural strength to the housing 140 and may meet at the intersection between the wall 142 and bottom surface 143. Alternative embodiments that do not include some or all of the aforementioned ribs are nevertheless within the scope of the present invention.

According to one embodiment, housing 140 is surrounded by an outer layer 147 that allows for the transfer of heat out of the device and also prevents users from directly touching the surface of housing 140, which may become hot as a result of the oxygen-generating reaction. In one embodiment, the outer layer 147 has a series of perforations to allow air to circulate across the surface of housing 140. According to another embodiment, outer layer 147 may be formed from a mesh. According to a still further embodiment, housing 140 may include heat-exchanging surfaces such as fins to facilitate the transfer of heat away from the oxygen-generating reaction.

As shown in FIG. 2A, a valve support assembly 144 extends upward from the bottom surface 143. Valve support assembly 144 couples with the valve assembly 200, as will be explained below. As shown in FIGS. 2A-2C, support plate 160 sits on the shelves 148 of wall ribs 146 in the housing 140. The support plate 160 has an aperture in its center that lines up with aperture 124 in the housing lid 120 for insertion of the valve assembly 200. The support plate 160 is designed to support water reservoir 170. According to one embodiment, support plate 160 includes openings that reduce the weight of the device and reduce the amount of material required to manufacture the support plate. According to a further embodiment, instead of support plate 160, ribs 146 extend from wall 142 to provide support for the water reservoir 170.

As shown in FIG. 2B, before the device 100 is actuated, the water 175, catalyst 260, and oxygen-generating mixture 190 (comprised of adduct 191 and moderator 192) are all separated. Specifically, water is in water reservoir 170, catalyst 260 is in catalyst chamber 265, and oxygen-generating mixture 190 is in housing 140. After the device is actuated, as explained more fully below, the water 175, catalyst 260, and oxygen-generating mixture 190 will all be located within the housing 140, forming a liquid or semi-liquid composition. As shown in FIG. 2C, the volume of the reactants fills a portion of the housing 140. According to another embodiment, the valve support assembly 144 and housing 140 are configured so that when the device is placed on a horizontal surface, the level of the reactants in the housing 140 is below the bottom of the valve assembly 200. This will prevent, or limit, the amount of liquid entrained in the flow of gas through the valve assembly. According to another embodiment of the invention, the size and shape of the housing 140 is also designed so that if the device were placed on its side (i.e., so the valve assembly 200 is positioned horizontally) the level of reactants would remain below the location of the valve assembly 200, ensuring that reaction components are not entrained in the gas flow. In this regard, openings in the support plate 160 allow reactants to flow through the plate, thus increasing the volume of the housing below the level of the valve assembly that can hold the reactants in the event the device is tilted during use.

As shown in FIG. 2B, water reservoir 170 sealingly connects with flanges 214 and 216 on the valve assembly (see also FIGS. 3A-D and 4) so that the interior of the water reservoir 170 is capable of being in fluid communication with the valve assembly.

As shown in FIG. 5, located above the reservoir 170 is a gas-permeable, liquid-impermeable membrane 171. According to one embodiment of the invention, the membrane is hydrophobic. According to another embodiment, the membrane 171 is formed from Tyvek® by DuPont of Wilmington, Del. Other suitable materials for membrane 171 include Gore-Tex® by W. L. Gore, as well as perforated and microperforated liquid-impermeable films.

As shown in FIG. 1, the upper rim of housing 140 includes pins 139 that extend upward. The pins 139 engage with corresponding holes (not shown) in the lower rim of lid 120. Corresponding holes 137 in the edge of the water reservoir 170 and holes 138 in the edge of membrane 171 (not shown) fit over the pins 139 in housing 140. When the lid 120 is fitted on the housing 140, the pins 139 fix the edges of the reservoir 170 and membrane 171 to the rim of the housing 140. In an alternative embodiment, a flange (not shown) on the periphery of water reservoir 170 is heat-sealed to the rim of housing 140.

As shown in FIG. 1, the exterior surface of housing lid 120 is higher at the edges and slopes downwardly toward the central region, creating the oxygen-accumulation chamber 122 at the periphery region of the lid 120. The reduced profile in the center of housing lid 120 allows for the actuation handle 180 to not extend above the profile of the device 100, which may prevent accidental actuation when oxygen is not needed, which nonetheless renders the one-time-only device unavailable for a true emergent situation. In an alternative embodiment, the handle 180 extends above the lid 120, so that when the device 100 is viewed from the side the handle 180 is the topmost structure.

Figure 3B:
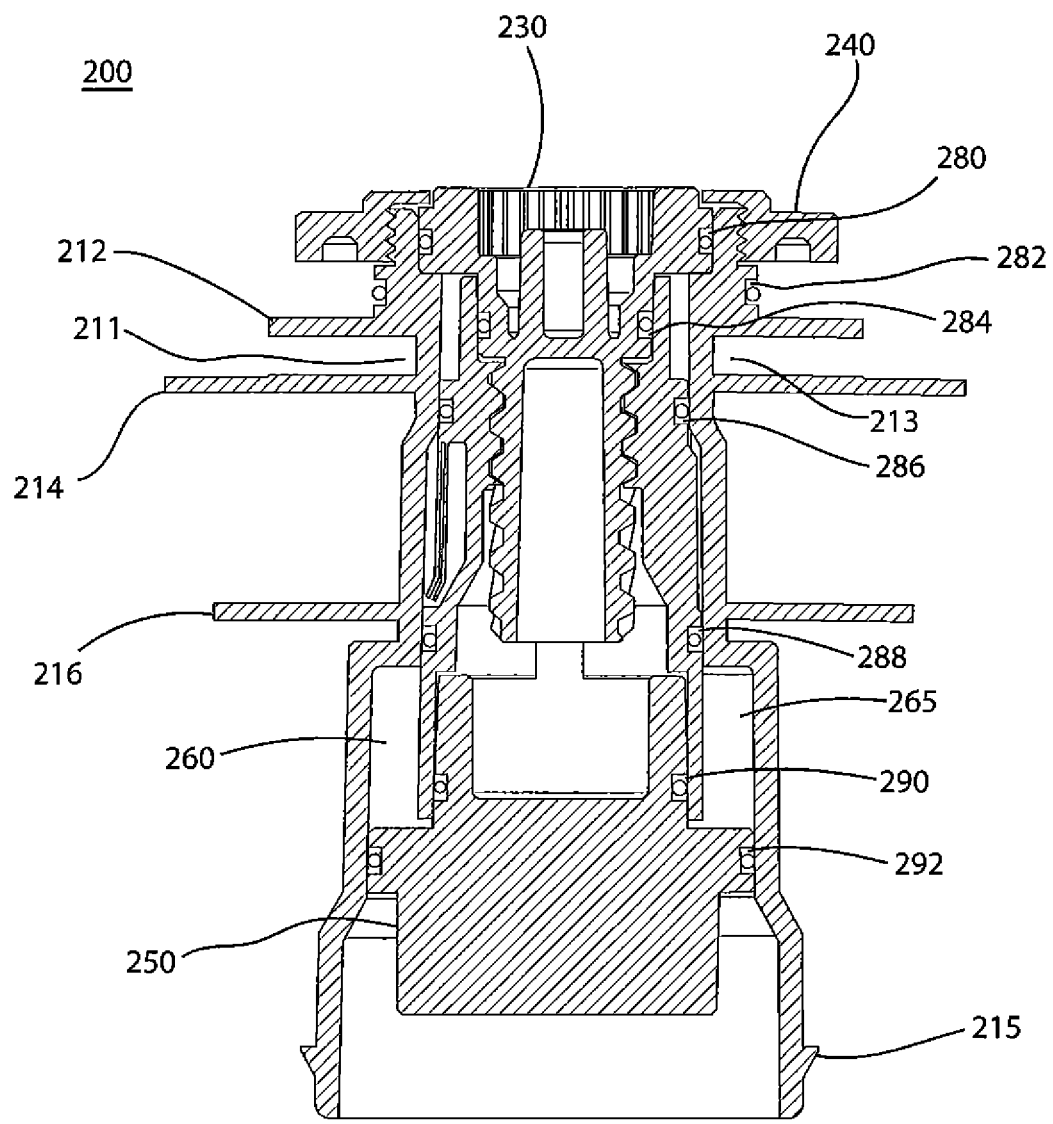
FIG. 3B depicts a cross-sectional view of the valve assembly of the oxygen delivery system of the present invention in the unactuated state.
Figure 3C:
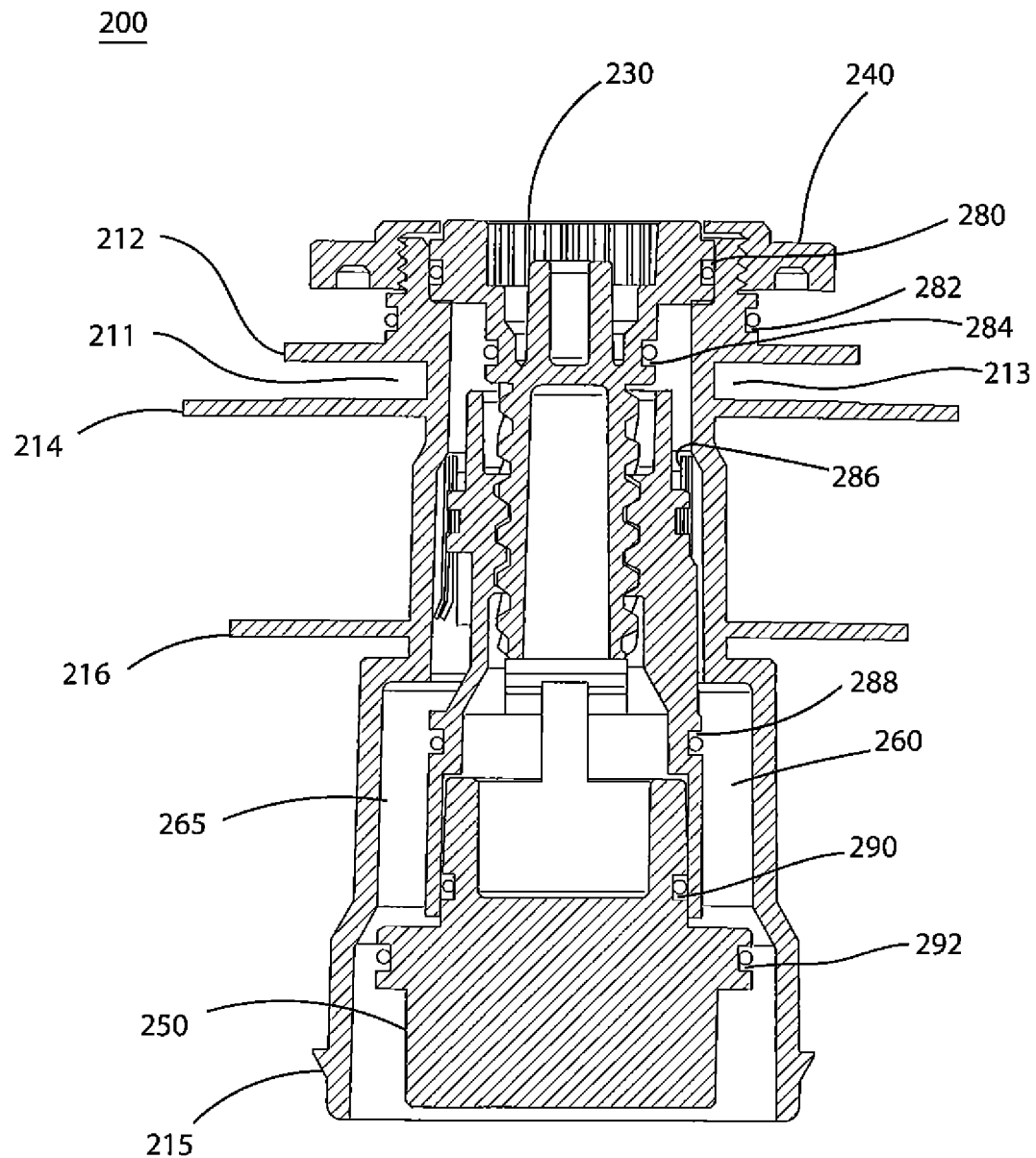
FIG. 3C depicts a cross-sectional view of the valve assembly of the oxygen delivery system of the present invention in the actuated state.
Figure 3D:
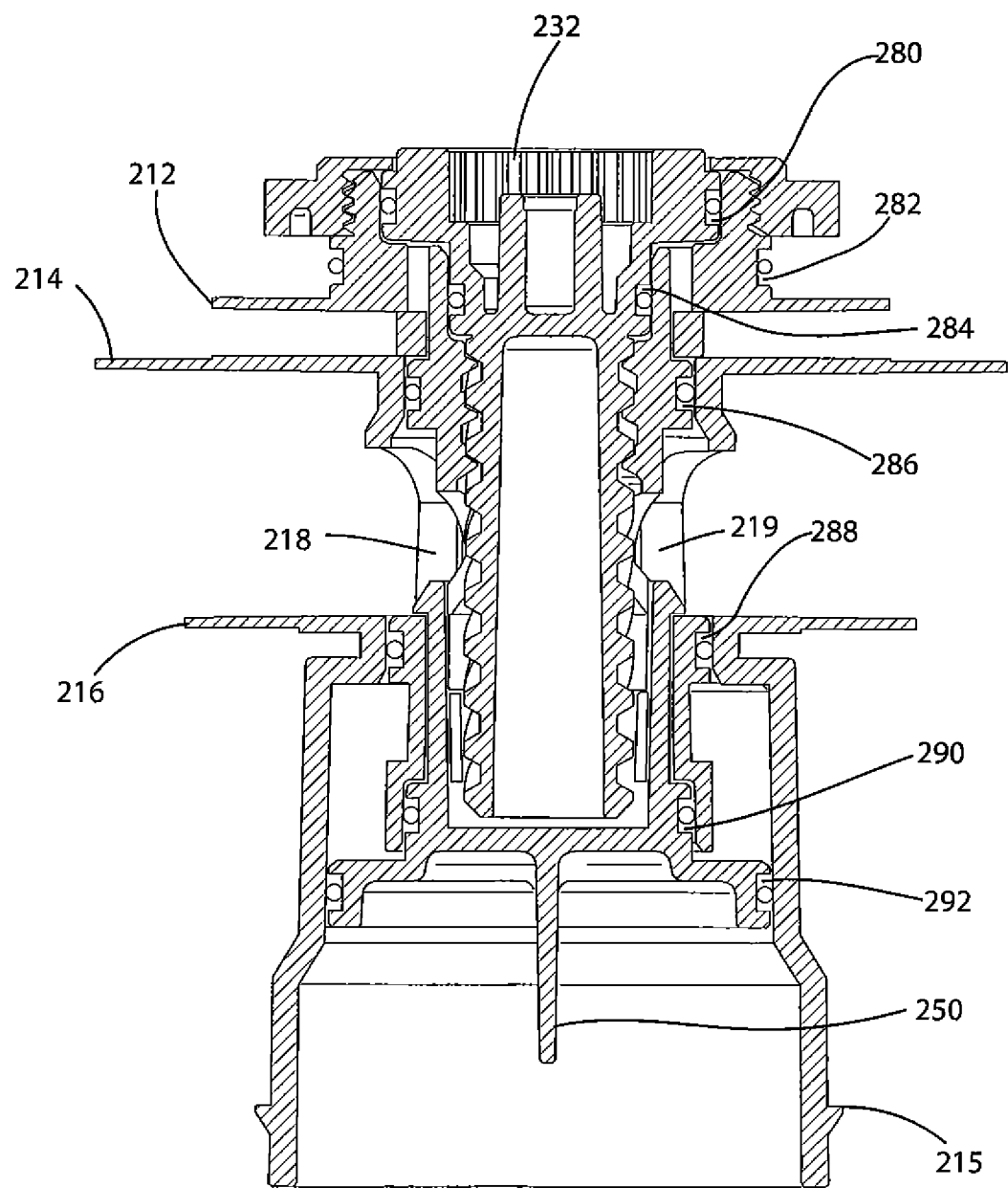
FIG. 3D depicts a cross-sectional view of the valve assembly of the oxygen delivery system of the present invention in the unactuated state.

A detailed description of the valve assembly 200, shown in FIGS. 3A-D, will now be provided. FIG. 3A is an exploded view of valve assembly 200. FIG. 3B is a cross-sectional view of valve assembly 200 before the device is actuated. FIG. 3C shows a cross-sectional view of valve assembly 200 when the device has been actuated. FIG. 3D is a cross-sectional rendering of valve assembly 200. As shown in FIG. 3A, valve assembly 200 is comprised of a valve body 210, valve 220, screw 230, nut 240, and cap 250. As shown in FIG. 3B, the valve 220 is positioned with the valve body 210.

As shown in FIG. 2A, valve assembly 200 is connected at its lower end with valve support assembly 144. The bottom of valve body 210 sits atop valve support assembly 144, which is located on and extends upward from the bottom surface 143 of housing 140. Valve support assembly 144 includes two extensions 154 and 156 that interlockingly engage with valve body tabs 215, snapping into slots 153 in valve support assembly 144. As described later, the valve assembly 200 is secured at its top to lid 120.

The top of valve body 210 has exterior threading 217 to engage with nut 240. As will be discussed below, a portion of valve body 210 extends through the hole 124 in the lid 120, and the nut 240 engages the threading 217 to affix valve assembly 200 to lid 120. The nut 240 secures the valve body 210 to the lid 120, and the interlocks 215 secure the valve body 210 to the bottom of the housing 140. This arrangement prevents the lid 120 and housing 140 from separating, for example, when internal gas pressure is generated inside the device.

Figure 4:
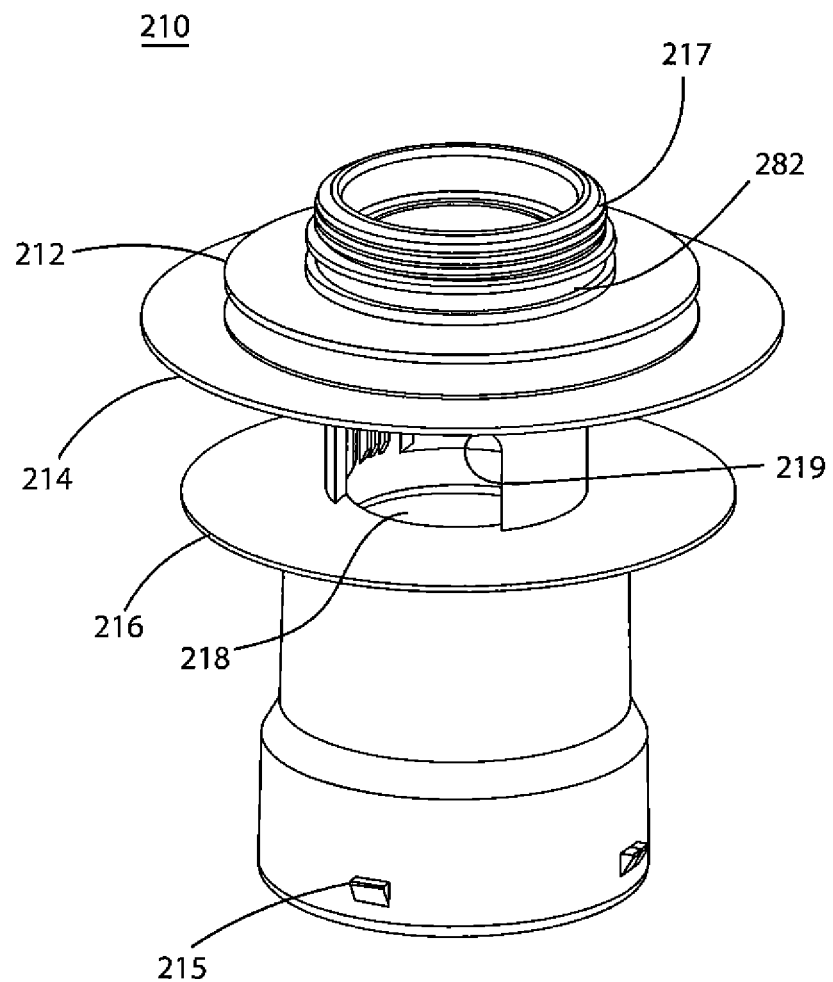
FIG. 4 depicts a perspective view of the valve body of the oxygen delivery system of the present invention.

As shown in FIG. 4, which is a detailed view of valve body 210, sealing flanges 212, 214, 216 extend radially from the exterior of valve body 210. When the device 100 is assembled, first sealing flange 212 engages its upper surface against membrane 171. According to one embodiment, as shown in FIG. 5, membrane 171 is trapped between the upper surface of flange 212 and a receiving surface on the bottom surface of lid 120.

The second sealing flange 214 and third sealing flange 216 are sealingly connected with upper and lower surfaces, respectively, of reservoir 170. The valve body 210 includes openings 218 and 219, on opposite sides of the valve body 210 between the second sealing surface 214 and the third sealing surface 216. Openings 218 and 219 allow water to enter into the interior space of valve body 210 and flow into the housing 140 when the oxygen-generation operation is actuated.

As shown in FIG. 3A, valve 220 is located between screw 230 on the top and cap 250 on the bottom. Valve 220 and cap 250 are connected and move together, as an integral unit. Valve 220 is generally cylindrical in shape, although the diameter in its top half is narrower than the bottom. Valve 220 has two apertures 228 and 229 that are opposite each other in the valve's side walls. As shown in FIG. 3D, these apertures are positioned adjacent apertures 218 and 219 of the valve body 210. As detailed below, apertures 228 and 229 allow water from water reservoir 175 to pass through to the interior of the valve housing 210 when the device is actuated. Also, as shown in FIGS. 3B and 3C, openings 211 and 213 are provided in the valve housing 210 between flanges 212 and 214. As will be discussed below, when the device is actuated, openings 211 and 213 allow generated oxygen to flow out of the valve 200.

The upper portion of the interior of valve 220 is threaded. The threads of valve 220 engage threads on the outer surface of screw 230. The top portion of screw 230 rests in a groove at the top of valve body 210 and is captive below a shoulder of nut 240. Thus, screw 230 is fixed in the vertical direction with respect to the valve assembly 200. When the device is actuated, screw 230 rotates. The engagement of the threads of valve 220 with the screw 230 cause the valve 220 to travel downwardly along the threads of screw 230, resulting in a short downward vertical displacement by valve 220 with respect to the valve body 210. FIG. 3C shows the valve assembly 200 after screw 230 has rotated to displace valve 220 with respect to valve body 210.

Cap 250 is sized and configured for insertion into the interior of the bottom of valve 220. As shown in FIG. 3A, cap 250 has two vertical posts 254, 256 that are integral with the rim at the top of cap 250; each post 254, 256 has a snap engagement at the respective top end. As shown in FIG. 3D, when the cap 250 is inserted into the valve 220, these snap engagements atop posts 254, 256 interlock with the lower edges of openings 228 and 229, respectively. Once so engaged, valve 220 and cap 250 are essentially a single unit that, as detailed below, move and operate together inside the valve body.

Valve assembly 200 functions to provide gas- and liquid-tight seals between regions of the device so that components of the oxygen-generating device are held separately until such time as oxygen is required and so that the interior of the device is protected from exposure to the outside environment when the device is in the unactuated state. As shown in FIGS. 3B-D, o-rings located in slots formed on the valve body 210, valve 220, screw 230, and cap 250 provide these seals. A first o-ring is held in slot 280, formed about the circumference of the head of screw 230. This o-ring is seated between the top of screw 230 and the interior of the valve body 210 to prevent generated oxygen from exiting the housing lid 120 and also to prevent outside air—and especially outside moisture—from entering the device during storage.

A second o-ring is held in slot 282 on the outside surface of valve body 210. This o-ring is seated between valve body 210 and the edge of opening 124 of housing lid 120 to both prevent generated oxygen from escaping through opening 124 and seal the interior of the device from outside gas and moisture.

A third o-ring is held in slot 284 on the outer surface of screw 230. This o-ring is seated between screw 230 and the interior of valve 220 to both prevent generated gas from escaping through the interior of the valve assembly 200 and prevent water 175 from leaking out of reservoir 170 through the interior of valve 220 when the device 100 is in the unactuated state.

A fourth o-ring is held in slot 286, formed on the surface of valve 220. This o-ring is seated between valve 220 and the interior of valve body 210 above openings 218, 219, 228, and 229 to prevent water 175 from leaking out of reservoir 170 when the device 100 is in the unactuated state.

A fifth o-ring is held in slot 288, formed in the surface of valve 220. This o-ring is seated between valve 220 and valve body 210, below openings 218, 219, 228, and 229, and below flange 216. This o-ring prevents water 175 from traveling through the valve assembly 200 when the device is in its unactuated state. This o-ring also forms a seal above catalyst chamber 265 and keeps the catalyst 260 separated from the water 175 when the device is in the unactuated state.

A sixth o-ring is held in slot 290, formed on the outer surface of cap 250. This o-ring is seated between cap 250 and the interior of valve 220 and isolates the catalyst 260 from the interior of the valve 220.

A seventh o-ring is held in slot 292, formed on the outer surface of the cap 250. This o-ring is seated between cap 250 and the interior of valve body 210 and seals the catalyst 260 and catalyst chamber 265 from the housing 140 when the device is in the unactuated state.

FIG. 3C shows the valve assembly 200 in its actuated state after screw 230 has rotated, driving valve 220 downward with respect to valve body 210. The o-ring in slot 280 maintains a seal between screw 230 and valve body 210. Likewise, the o-ring in slot 282 maintains a seal with lid 120. As a result, gas generated in the housing 140 is prevented from escaping through the opening 124 in lid 120 and, instead, flows into chamber 122 and exits from the oxygen port 125.

Displacement of the valve 220 during actuation disengages both the o-rings in slots 284, 286, and 288 from between the valve 220 and valve body 210 and the o-ring in slot 292 from between the cap 250 and the interior of valve body 210.

As shown in FIG. 1, the valve assembly 200 is connected at its top end with the circular opening 124 of the housing lid 120. The valve body's threaded end 217 is inserted through opening 124. Nut 240 engages the threaded end, pulling the upper end of the valve assembly against the lower surface of the lid 120. Handle 180 is connected with the top of screw 230 of the valve assembly 200. Handle 180 has an aperture 182 in its center that allows the handle 180 to be connected with the valve assembly 200 by a screw 188 that is inserted through the aperture 182 into a threaded aperture 231 in the top of screw 230. According to one embodiment, ribs 232 on the inside surface at the top of screw 230 engage with corresponding ribs on a projection on the lower side of the handle 180 (not shown) to communicate rotational force from the handle 180 to the screw 230.

Figure 7:
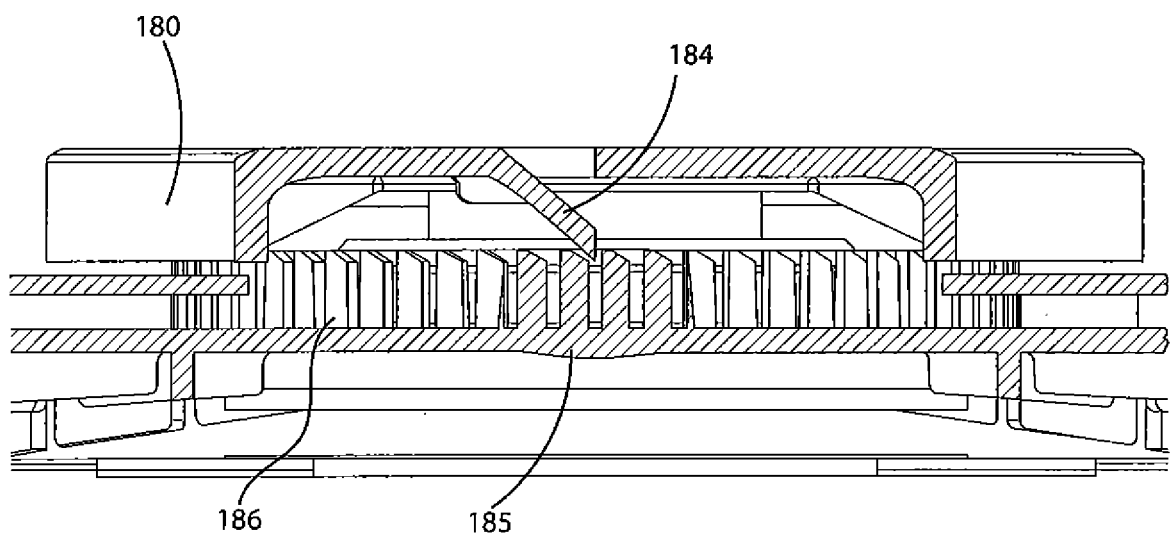
FIG. 7 depicts a cross-sectional view of the ratchet on the device lid and the corresponding pawl on the underside of the actuation handle.

As shown in FIG. 1, there is a circular ratchet 185 that is concentric with, but outside of, circular opening 124. As shown in FIG. 7, ratchet 185 is comprised of a plurality of spaced-apart individual teeth 186. FIG. 7 also shows a detailed view of the ratchet 185 and handle 180. The ratchet 185 is sized to be concentric with, but have a diameter less than, the handle 180. The ratchet is further sized so that the individual teeth will engage with a pawl 184 on the underside of the handle 180. The pawl 184 and teeth 186 are configured such that the pawl 184 engages and passes each individual tooth 186 when traveling in one direction, e.g., clockwise, but that once the pawl 184 passes a tooth 186 the pawl 184 may not be reversed, e.g., travel counterclockwise past the tooth 186 just engaged. In the present invention, this configuration ensures that once the oxygen generation process begins by actuating the handle 180, there is no reversing the handle 180 or the process. This is critical insofar as the device is single-use only, and an observer will be able to ascertain quickly whether the device 100 of the present invention has been used or is available.

The arrangement and selection of chemical reactants in the device when it is in its unactuated state, according to one embodiment, will now be described. The reactant components are held in separate compartments, sealed from one another and from the outside environment when the device is in the unactuated state.

As shown in FIG. 2B, water 175 is held in water reservoir 170. The reservoir 170, according to one embodiment, is made of a flexible, water-impermeable material such as silicon, low density polyethylene, polypropylene, aluminum, polycarbonate, or the like. According to one embodiment, when the device is actuated, the reservoir collapses as water drains out of it. The reservoir 170 surrounds the valve assembly 200 and is sealed with flanges 214 and 216 of the valve assembly 200, as discussed above. The flexible reservoir is supported by plate 160. The reservoir 170 is in liquid communication with openings 218 and 219 of the valve assembly. In the unactuated state, the water 175 is prevented from flowing through the valve assembly 200.

Within the valve assembly, catalyst chamber 265 holds the catalyst 260, which is sealed within that chamber by o-rings in slots 288 and 292. The catalyst 260 is selected from a variety of peroxide-decomposing catalysts, including metal oxides, e.g., oxides of aluminum, cobalt, iron, platinum, titanium, and silver. Preferably, the catalyst 260 is powdered manganese dioxide ("$MnO_2$") with particle size of the $MnO_2$ being preferably between about a diameter of 5 µm and about 500 µm. According to another embodiment, the catalyst 260 is activated $MnO_2$, i.e., $MnO_2$ that has been subjected to a series of heat/oxygen/inert gas treatments that skilled artisans use to produce an $MnO_2$ powder that is especially active as a peroxide-decomposing catalyst 260.

The $MnO_2$ is provided in an amount effective to catalyze the decomposition of hydrogen peroxide and produce the desired volume of $O_2$ with regard to the types and amounts of the other reaction compounds. The amount of $MnO_2$ used in the composition also depends on the mesh size of the $MnO_2$ and on the degree of activation of the $MnO_2$. Such activated $MnO_2$ powders are also very active in the decomposition of hydrogen peroxide, and while activated $MnO_2$ powders can be used in the compositions of the disclosure, their use is not required.

Below the valve assembly 200 in housing 140 is the oxygen-generating mixture 190, comprising a hydrogen peroxide adduct 191 and a temperature-stabilizing material 192.

The amounts of water 175, oxygen-generating mixture 190, and catalyst 260 are selected to achieve a desired rate and amount of oxygen generated to provide adequate amounts of gas for a particular purpose, for example, to administer oxygen to a patient in respiratory distress. As discussed above, the size and shape of the housing 140 is selected so that the total volume of the mixture will not contact the lower end of the valve assembly 200 when the device is in its normal, horizontal orientation. The amount of reactants and the size of the housing are also selected so that should the physical orientation of the device change, e.g., the device being turned on its side so that the exterior surface of the bottom of housing 140 is no longer the surface had been placed on for actuation, the reactant mixture will not reach the valve assembly 200.

The hydrogen peroxide adduct 191 is a compound that will react with water to generate hydrogen peroxide. This hydrogen peroxide then decomposes to oxygen and water when it interacts with the catalyst 260. Suitable compounds may be adducts of hydrogen peroxide, including sodium carbonate and hydrogen peroxide, urea and hydrogen peroxide, and the like. According to a preferred embodiment, the adduct 191 is sodium carbonate and hydrogen peroxide. According to a most preferred embodiment, the adduct 191 is NaPerc, an adduct of sodium carbonate and hydrogen peroxide with an empirical formula $Na_2CO_3$-$1.4H_2O_2$.

The temperature-stabilizing material 192 dissolves endothermically in water. Preferably, such an agent has a heat of dissolution selected to limit the temperature of the oxygen-generating reactions below a suitable maximum temperature. Suitable temperature stabilizing materials include, for example, trisodium phosphate dodecahydrate, sodium tetraborate decahydrate, disodium phosphate heptahydrate, disodium phosphate dodecahydrate, and combinations of the foregoing. According to a preferred embodiment, the cooling agent is trisodium phosphate dodecahydrate ("TSP") having the formula $Na_3PO_4$-$12H_2O$ and a cooling capacity of 40.25 cal/g.

The rate of dissolution of TSP, and hence the amount of cooling in the reaction, has been found to be affected by the TSP form. The reaction profile of TSP powder and small TSP tablets differs, and thus TSP can be used as a powder, a tablet, a capsule, or combinations thereof, with the form selected being based on the desired reaction profile. For example, TSP powder dissolves more quickly than TSP tablets, resulting in more robust cooling of an exothermic reaction; the oxygen-generating reaction according the present invention being an example. In some embodiments, TSP is used as a tablet and/or a capsule, either alone or in combination with TSP powder. According to a preferred embodiment, TSP tablets with a diameter of about 0.63 cm to about 0.97 cm and a thickness of about 0.31 cm to about 0.50 cm are used. The TSP tablet faces may have flat or slightly outwardly curved profiles. According to yet another embodiment, the powder, tablets, or capsules may include other compounds, such as waxes, e.g., paraffin, which may also affect the rate of dissolution.

As discussed earlier, this disclosure relates to a portable chemical oxygen generator. The oxygen generated is the result of a chemical process involving the combination of several chemical components. By storing the components of the oxygen-generating reaction in separate, sealed compartments, and by protecting those components from environmental moisture, the device can be stored in the unactuated state for long periods of time, preferably longer than one month, one year, two years, and three years at 10° C. to 27° C.

Because the rate of reaction is controlled by adjusting the rate of dissolution of the temperature-stabilizing material 192, the maximum temperature of the device during operation can be controlled to remain preferably below 100° C., more preferably below 80° C., and most preferably below about 50° C. Also, by selecting reaction components according to an embodiment of the invention, oxygen can be produced in emergent situations without toxic by-products or volatile organic compounds—the result being these compositions generating high-purity, breathable oxygen.

One aspect of the disclosure is to an oxygen-generating composition including NaPerc, $MnO_2$, TSP, and water. In an alternative embodiment, the water in the composition may also include antifreeze, e.g., polyethylene glycol.

Another aspect of the invention is a method of generating breathable oxygen that includes bringing an oxygen-generating composition of the disclosure into contact with water. According to one embodiment of the invention, the device generates oxygen that qualifies for labeling as "Oxygen, USP"—meaning that the generated oxygen meets the United States Pharmacopoeia standard. The amount of water 175, catalyst 260, adduct 191, and the amount and physical configuration of the temperature-stabilizing material 192 can be selected such that oxygen is generated at a rate of at least 1 L/min, at least 2 L/min, at least 3 L/min, at least 4 L/min, or at least 6 L/min for periods of 15 minutes, 20 minutes, 30 minutes, 45 minutes, or 90 minutes (calculated based on 90 L volume). Further, the oxygen-generating composition of the disclosure can be prepared such that one or more of foam, toxic by-products, and volatile organic contaminants are minimized when the device is actuated. According to one embodiment of the invention, the oxygen generated by the device meets the Environmental Protection Agency's air quality standards for levels of VOCs (i.e., Volatile Organic Compounds) present.

The disclosure further provides a method of generating oxygen including contacting an oxygen-generating composition of the disclosure with water. As used here, "contacting" can include any of flowing the water past/through/into the oxygen-generating composition or immersing the oxygen-generating composition in the water. In some embodiments, the contacting will occur by opening a valve in an upper compartment containing water and a lower compartment containing the oxygen-generating composition and allowing gravity to drain the water into the lower compartment to initiate the reaction and release of oxygen. The relative amounts of NaPerc, $MnO_2$, and TSP used in the method of generating oxygen can be any amounts disclosed here for the oxygen-generating composition.

On contact with the water, the NaPerc adduct 191 decomposes to produce sodium carbonate and hydrogen peroxide. The hydrogen peroxide further decomposes to water and oxygen upon contact with the $MnO_2$, i.e., catalyst 260. The decomposition rate of hydrogen peroxide depends on the concentration of the hydrogen peroxide and on the reaction temperature. In various embodiments, the $MnO_2$ present is in an excess to overwhelm the hydrogen peroxide with an abundance of catalyst 260. In some embodiments, an amount of $MnO_2$ provided in the range of about 0.3% to about 1% of the weight of NaPerc adduct 191 is sufficient to react the $H_2O_2$ produced at a substantially instantaneous rate such that $H_2O_2$ is decomposed to oxygen as quickly as the $H_2O_2$ is released from the decomposition of NaPerc adduct 191. In such embodiments, the rate of production of oxygen is substantially equivalent to the rate of decomposition of the NaPerc adduct 191 and the concentration of $H_2O_2$ in the aqueous phase of the reaction remains at all times at exceedingly low concentrations. For this reason, the exiting oxygen stream is also substantially free of $H_2O_2$.

In a preferred embodiment of the present invention, water flows from an upper sealed compartment through a catalyst chamber 265 in valve 220, mixing with the catalyst 260 and exiting the valve assembly 210 as an aqueous-$MnO_2$ catalyst combination, whereupon it contacts the NaPerc adduct 191 and TSP cooling agent 192 that are pre-located in the housing 140. The NaPerc adduct 191 decomposes to produce sodium carbonate and hydrogen peroxide, with the hydrogen peroxide further decomposing to water and oxygen because of contact with the $MnO_2$ catalyst 260.

The oxygen-generating composition 190, catalyst 260, and the water 175 can be provided in any amounts suitable for initiating and maintaining the oxygen generation reaction.

As noted earlier, there are situations where individuals are in respiratory distress and need oxygen immediately. The present invention addresses that problem by providing contaminant-free oxygen within a short time after the portable oxygen generation device described and claimed here is actuated. In operation, oxygen is generated by using the portable chemical oxygen generator of the present invention in proximity with the individual needing oxygen, so that once flowing a patient may begin to breathe the oxygen via a mask or nasal cannula in fluid communication with the device.

Figure 6B:
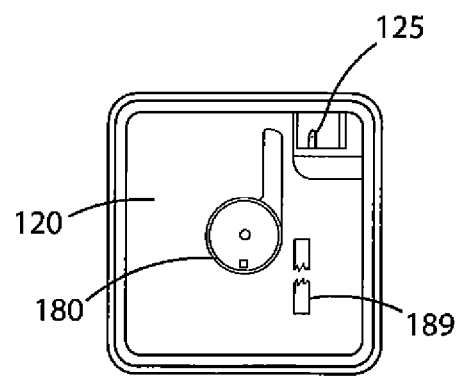
FIG. 6B depicts a top view of the oxygen delivery system of the present invention and further depicts the actuation handle in the actuated state.

The oxygen generation process takes place in the device of the present invention as follows. The process begins by placing the device on a generally-horizontal surface. The user first removes a restraint 189 that is placed on the actuation means and then rotates the actuation means (e.g., a handle 180) approximately 270°, the same arcuate path as moving a clock's minute hand from the 12:00 to 9:00 position (see FIGS. 6A and 6B). The restraint 189 prevents accidental actuation of the handle 180 and alerts a user when the device has previously been activated (and thus rendered unusable). The handle 180 is connected with valve assembly 200, which is underneath the lid 120. Before actuation the valve assembly 200 is sealed off from, but adjacent, several other sealed compartments, namely, the oxygen-accumulation chamber 122 underneath the lid 120, the water reservoir 170, and the housing 140 beneath the support plate 160.

Figure 3E:
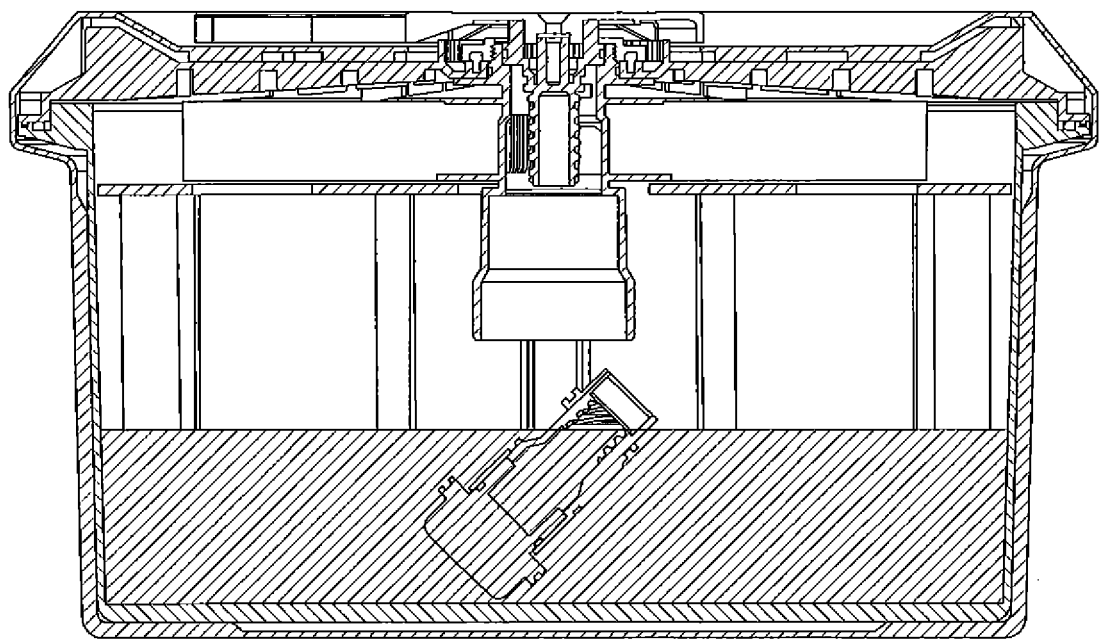
FIG. 3E depicts a cross-sectional view of an embodiment of the oxygen delivery system of the present invention in which the valve and cap separate and drop from the valve body into the housing after actuation.

Actuation of the handle 180 causes the downward displacement of the valve 220 and cap 250 with respect to valve body 210, as shown in FIG. 3C. This displacement disengages o-rings in slots 284, 286, 288, and 292 on valve 220 away from the surface of valve body 210. Water 175 from reservoir 170 flows through openings 218 and 219 through the holding chamber 265, taking catalyst 260 along as it flows downward into housing 140. This arrangement assures that the catalyst 260 is delivered into the reaction mixture. In one embodiment, shown in FIG. 3E, after actuation the valve 220 travels down the entirety of the threading of screw 230 and separates from the screw, such that valve 220 and cap 250 drop from the interior of valve body 210 into the housing 140, along with water 175 and catalyst 260. One additional benefit is that this assures the likelihood that all of catalyst 260 is present with the water 175 and oxygen-generating mixture 190 to optimize the reaction in housing 140.

The previously described oxygen generation chemical reaction then occurs. Generated oxygen and water vapor flow upward through the valve assembly 200, out through holes 211 and 213 of the valve housing 210, and into the space between the top surface of the reservoir 170 and the bottom surface of the membrane 171. Oxygen flows through the liquid-impermeable, gas-permeable membrane 171 into the collection chamber 122 and then out of the device 100 via oxygen port 125. Membrane 171 serves to prevent the reaction mixture from passing into the collection chamber 122, and further prevents liquid from exiting the device.

Figure 8:
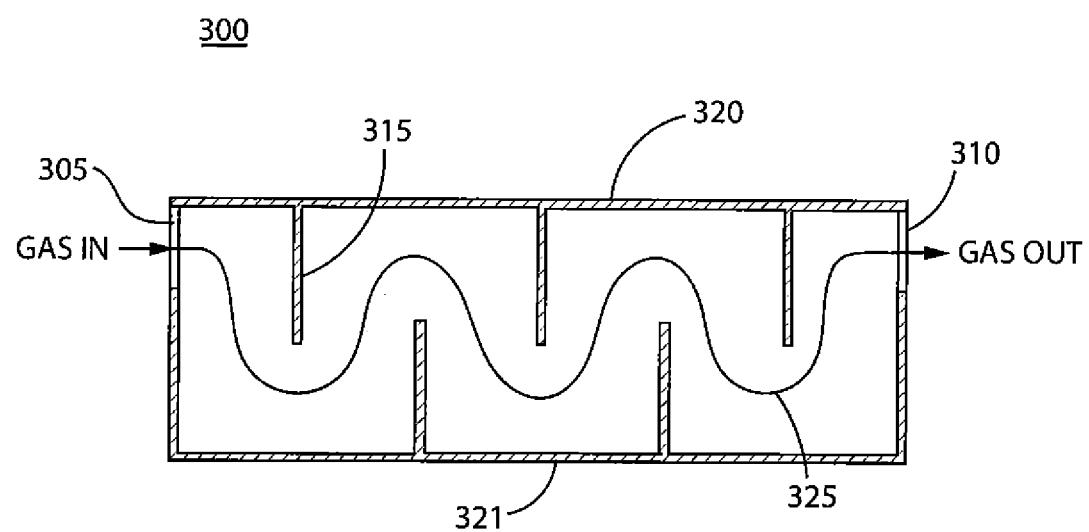
FIG. 8 depicts the top view of the interior of a water trap of the present invention and the flow path of gas through the trap.

The generated oxygen that flows out of the device 100 at oxygen port 125 includes water vapor and may well be above ambient temperature. To reduce the condensation that may exit the tubing into the mask or nasal cannula, which may be unpleasant for a patient, a water trap 300 for collecting condensate is shown in FIG. 8. The water trap 300 is interposed between the outlet port 125 (see FIG. 1) and the mask or nasal cannula (not shown). In one embodiment, the water trap 300 is formed of heat-sealable and gas-tight flexible barrier materials, e.g., CADPAK HD100 packaging material by Cadillac Products Packaging Co. of Troy, Mich. According to an embodiment of the invention, the material likewise has high thermal conductivity. The water trap 300 has an inlet 305 connected with oxygen port 125 and an outlet 310 connected with a tube that is connected on its other end with the mask or cannula. The water trap 300 simultaneously provides a pathway for the generated oxygen while trapping condensation.

Figure 9:
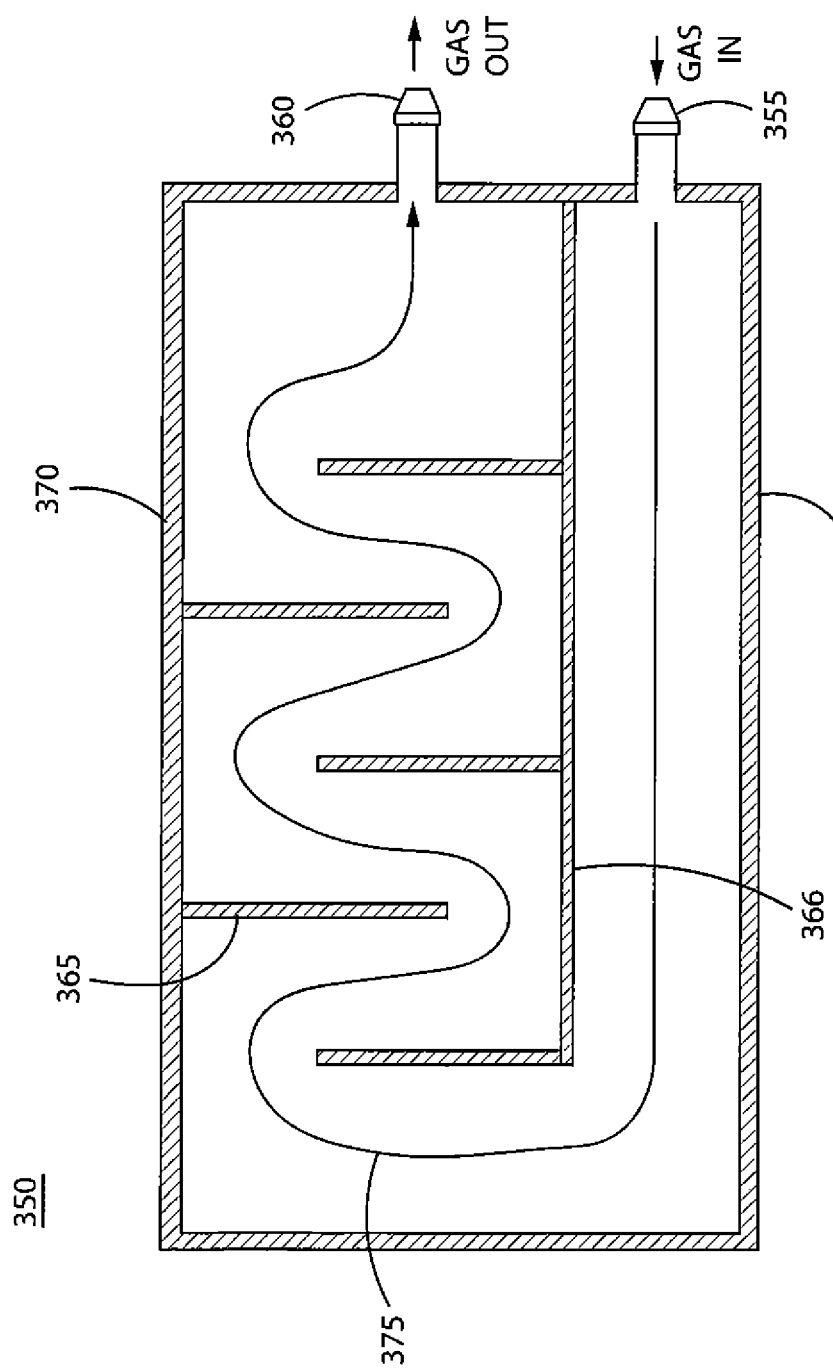
FIG. 9 depicts the top view of the interior of an alternative embodiment of a water trap and the flow path of gas through the trap.

According to one embodiment, the water trap 300 has a series of vertical internal barriers 315 that are staggered on opposite sides, with each such barrier projecting more than half the distance from one interior sidewall 320 of the water trap 305 to the other interior sidewall 321. This configuration ensures that oxygen passing through the trap travels a path 325 that if laid out on a straight line would be longer than the length of the water trap 300 itself. This elongated path 325 has the added benefit of allowing for the collection of more condensate than the straight path alone. In addition, the longer flow path enhances cooling the generated gas closer to ambient temperature, thus increasing the amount of moisture condensed from the gas stream and reducing unwanted condensation in the tube leading to the mask or cannula. In one embodiment of the invention, the water trap 300 is generally rectangular in shape. In the embodiment shown in FIG. 8, the water trap 300 has an inlet 305 on one end and an outlet 310 on the other end. In another embodiment, shown in FIG. 9, the water trap 350 has an inlet 355 and an outlet 360 on the same side, with an internal barrier 366 that runs generally parallel to the sidewalls 370, 371 but closer to sidewall 371. The internal barriers 365 are staggered between interior sidewall 370 and internal barrier 366, which runs generally perpendicular to internal barrier 365. In this embodiment, the oxygen generated enters from inlet 355 and travels through the water tap 350 along flow path 375, which runs the length of internal barrier 366 before traveling through the area defined by staggered internal barriers 365 and eventually exiting the water trap 350 at outlet 360. This longer flow path allows for more condensation to be captured.

According to one embodiment, a first length of tubing extends from the device's oxygen port 125 to inlet 305 of water trap 300 and a second length of tubing extends from outlet 310 to a mask or cannula. The first length of tubing may be long enough that when the device is used the water trap 300 is positioned away from the housing 140 so that it is not heated by the oxygen-generating reaction.

For access and use by a patient needing oxygen, the device 100 of the present invention may be stored by itself (without a tube, face mask/nasal cannula, and/or water trap pre-connected, but in close proximity). The device 100 may also be stored with a tube and face mask/nasal cannula, the tube preferably being pre-connected with oxygen port 125. In another embodiment, the device 100 may have two tubes, the first tube being pre-connected with oxygen port 125 on the first tube's proximal end and with water trap inlet 305 on the first tube's distal end and the second tube being pre-connected with water trap outlet 310 on the second tube's proximal end and with the face mask/nasal cannula on the second tube's distal end.

Figure 10:
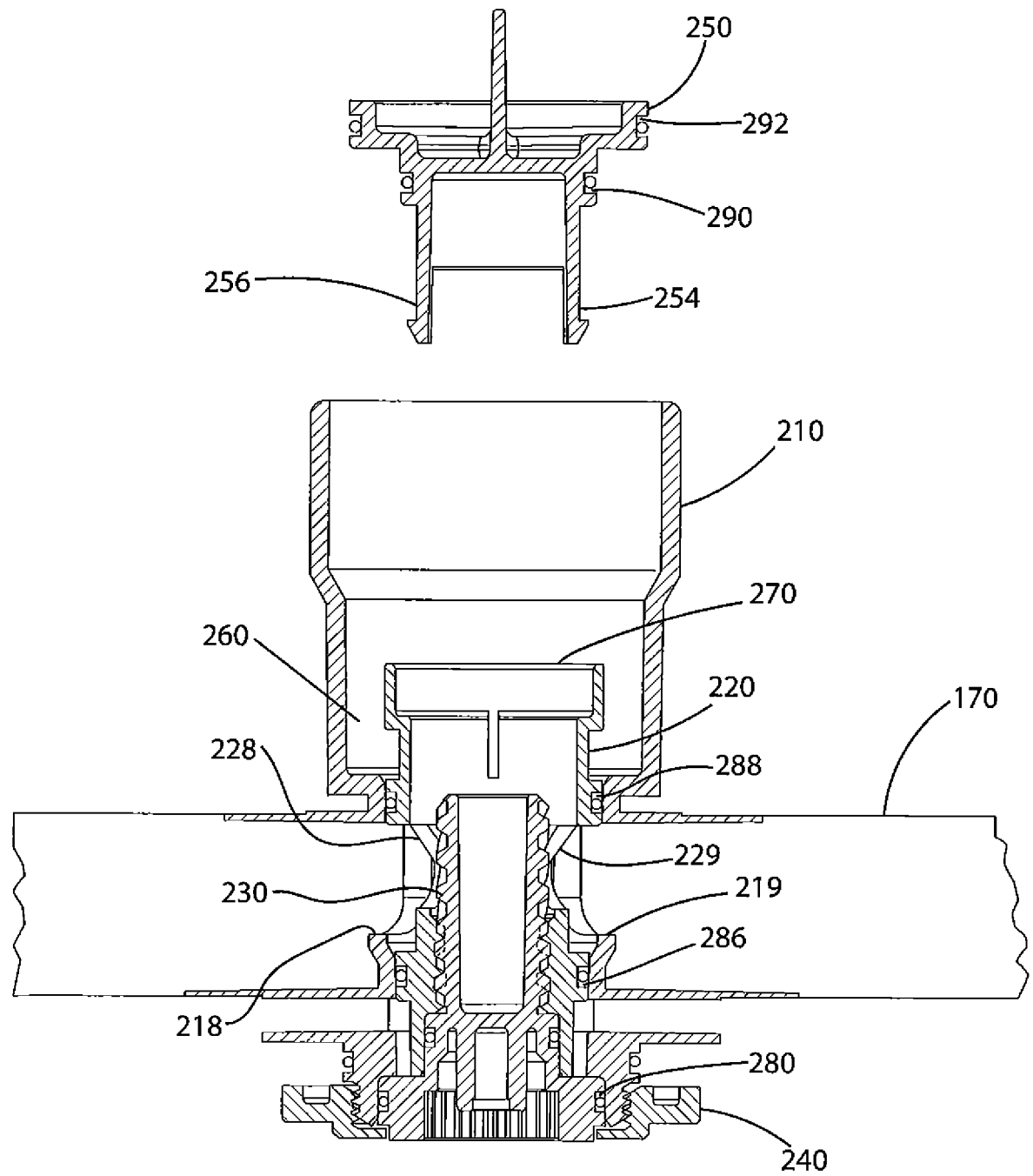
FIG. 10 depicts a partially assembled valve and reservoir according to a further embodiment of the invention.

An oxygen generator according to an embodiment of the present invention may be assembled as follows. Valve housing 210 is connected with a reservoir 170 by heat sealing flanges 214 and 216 to upper and lower surfaces of the reservoir. Valve assembly 200 is then partially assembled as shown in FIG. 10 (with the valve assembly 200 inverted as will be explained below).

As part of the assembly of valve 200, valve body 220 is inserted into valve housing 210 so that the o-rings disposed in flanges 286 and 288 engage the interior surfaces of the valve housing 210 as discussed above with regard to FIG. 3B. Screw 230 is threaded into valve body 210. The o-rings in slots 280 and 284 engage interior surfaces of the valve housing 210 and valve body 220, respectively. At this stage, cap 250 is separate from valve body 220. Note that openings 228 and 229 in valve body 220 (shown more clearly in FIG. 3A) are in fluid communication with openings 218 and 219 of valve housing 210 and thus also in fluid communication with reservoir 170. Also, the interior of valve body 220 is hollow so that opening 270 of valve body 220 is also in fluid communication with the reservoir 170 via openings 218, 219, 228, 229. Also, catalyst chamber 260 is partially formed above the o-ring in slot 288. The catalyst chamber 260 is open at its upper end through the interior of valve housing 210.

The reservoir 170 is then filled with a predetermined amount of aqueous solution 175. The solution is introduced through opening 170 in valve body 220 and flows through the interior of valve body 220 and through openings 218, 219, 228, 229 into reservoir 170. Catalyst 265 is delivered to the partially formed catalyst chamber 260 through the open end of valve housing 210. Cap 250 is then inserted into the open ends of valve housing 210 and valve body 220. Snap engagements on posts 254 and 256 engage edges of openings 228 and 229 to fix the cap 250 with respect to the valve body 220. O-rings in slots 290 and 292 on the cap 250 sealingly engage with interior surfaces of the valve body 220 and valve housing 210, respectively. As a result, the aqueous solution 175 is prevented from flowing through the valve 200 and the catalyst 265 is sealed within the catalyst chamber 260, preventing any interaction of the solution 175 and catalyst 265 until the device is actuated. When the valve assembly 200 and reservoir 170 are positioned right-side up, the valve 200 is in the configuration shown in FIG. 3B.

The device is further assembled as follows. A predetermined amount of the oxygen-generating mixture 190 is placed on the bottom of housing 140. As shown in the exploded view of FIG. 1, support plate 160 is positioned in housing 140 and rests on the shelves 148 formed by the upper ends of ribs 146. Valve assembly 200 is inserted through a hole in the center of the support plate 160 and tabs 215 on the lower portion of valve housing 210 engage with extensions 154 and 156 of valve support assembly 144 by snapping into slots 153, as discussed with respect to FIG. 2A.

The edge of reservoir 170 is engaged with the rim of housing 140. According to one embodiment, as shown in FIG. 1, holes 137 along the edge of reservoir 170 are fitted over pins 139 along the rim of housing 140. According to another embodiment, the edge of reservoir 170 is heat sealed to the rim of housing 140.

Lid 120 is fitted over the edge of housing 140 with the upper portion of valve 200 extending through opening 124 in lid 120. Nut 240 is threaded onto the top of valve assembly 200, securing valve assembly 200 to the lid 120. Because valve assembly 200 is fixed to the bottom 143 of housing 140 by the valve support 144 and to the lid 120 by nut 240, the valve assembly 200 provides structural support to hold the lid 120 against the housing 140. As a result, forces due to increased gas pressure will not cause the lid 120 to detach from housing 140 when oxygen is generated. Handle 180 is then connected with screw 230 of the valve assembly 200. A machine screw 188 is inserted through a hole in the handle and secures the handle 180 to the valve assembly 200 to allow the device to be actuated as described above. According to one embodiment, a restraint 189 such as an adhesive label is applied to the handle 180 and lid 120.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

We claim:

1. A portable chemical oxygen generator comprising:
   a housing;
   a reaction chamber within the housing;
   a valve in fluid communication with the reaction chamber;
   an internal chamber within the valve, the internal chamber being formed by releasable seals;
   a reservoir in fluid communication with the valve; and
   a valve actuator, wherein operation of the valve actuator creates a fluid path from the reservoir through the internal chamber into the reaction chamber.

2. The generator of claim 1, further comprising an outlet path through the valve and out of the generator when the valve is actuated.

3. The generator of claim 2, further comprising a membrane disposed in the outlet path.

4. The generator of claim 1, wherein the valve actuator comprises a threaded, rotatable shaft and the valve comprises a threaded valve portion engaged with the threaded rotatable shaft, wherein the valve is actuated by rotation of the shaft.

5. The generator of claim 4, wherein the valve actuator further comprises a ratchet mechanism, wherein the ratchet mechanism allows rotation of the shaft in a direction to actuate the valve.

6. The generator of claim 1, further comprising a restraint connected with the valve actuator.

7. The generator of claim 1, wherein the housing further comprises an outer layer.

8. The generator of claim 7, wherein the outer layer further comprises perforations.

9. The generator of claim 1, wherein the housing further comprises a heat exchanging structure.

10. The generator of claim 2, further comprising a condensate trap disposed at an outflow portion of the outlet path.

11. The generator of claim 1, wherein the valve enters the reaction chamber from above when actuated.

12. The generator of claim 1, wherein the reaction chamber holds an adduct.

13. The generator of claim 1, wherein the valve holds a catalyst.

14. The generator of claim 1, wherein the reservoir holds an aqueous solution.

15. The generator of claim 12, wherein the adduct is a peroxide adduct.

16. The generator of claim 15, wherein the peroxide adduct is sodium percarbonate.

17. The generator of claim 1, further comprising a temperature stabilizer in the reaction chamber.

18. The generator of claim 17, wherein the temperature stabilizer comprises one or more of a powder, a tablet, and a capsule.

19. The generator of claim 14, wherein the aqueous solution comprises water.

20. The generator of claim 13, wherein the catalyst is a metal catalyst.

21. The generator of claim 20, wherein the catalyst is manganese dioxide.

22. A method of generating oxygen using the generator of claim 1, the method comprising:
    generating oxygen using the generator.

* * * * *